United States Patent
Amano et al.

(10) Patent No.: US 7,998,087 B2
(45) Date of Patent: Aug. 16, 2011

(54) BLOOD TEST APPARATUS AND BLOOD TEST METHOD

(75) Inventors: Yoshinori Amano, Ehime (JP); Masaki Fujiwara, Ehime (JP)

(73) Assignee: PANASONIC Corporation, Osaka (JP)

( * ) Notice: Subject to any disclaimer, the term of this patent is extended or adjusted under 35 U.S.C. 154(b) by 389 days.

(21) Appl. No.: 12/162,627

(22) PCT Filed: Jan. 31, 2007

(86) PCT No.: PCT/JP2007/051627
§ 371 (c)(1),
(2), (4) Date: Jul. 30, 2008

(87) PCT Pub. No.: WO2007/088905
PCT Pub. Date: Aug. 9, 2007

(65) Prior Publication Data
US 2009/0177117 A1 Jul. 9, 2009

(30) Foreign Application Priority Data
Jan. 31, 2006 (JP) ................. 2006-022038

(51) Int. Cl.
*A61B 5/00* (2006.01)
*G01N 33/50* (2006.01)
*G01N 1/00* (2006.01)
*G01N 27/26* (2006.01)
*G01N 21/75* (2006.01)
*C12Q 3/00* (2006.01)

(52) U.S. Cl. .......... 600/583; 606/181; 204/403.01; 204/403.03; 422/400; 422/401; 422/402; 422/410

(58) Field of Classification Search .......... None
See application file for complete search history.

(56) References Cited

U.S. PATENT DOCUMENTS

| | | |
|---|---|---|
| 6,706,159 B2 | 3/2004 | Moerman et al. |
| 7,378,007 B2 | 5/2008 | Moerman et al. |
| 7,575,558 B2 * | 8/2009 | Boecker et al. ............... 600/573 |
| 2002/0130042 A1 | 9/2002 | Moerman et al. |
| 2004/0215224 A1 * | 10/2004 | Sakata et al. ................. 606/181 |
| 2005/0011759 A1 | 1/2005 | Moerman et al. |
| 2006/0129065 A1 * | 6/2006 | Matsumoto et al. .......... 600/583 |

FOREIGN PATENT DOCUMENTS

| | | |
|---|---|---|
| JP | 2003-524496 A | 8/2003 |
| WO | 2003/007819 A1 | 1/2003 |
| WO | 2004/054445 A1 | 7/2004 |

OTHER PUBLICATIONS

U.S. Appl. No. 12/159,904 to Fujiwara et al., filed Jul. 2, 2008.
U.S. Appl. No. 12/162,612 to Fujiwara et al., filed Jul. 30, 2008.
U.S. Appl. No. 12/278,825 to Amano et al., filed Aug. 8, 2008.

* cited by examiner

*Primary Examiner* — In Suk Bullock
*Assistant Examiner* — Jennifer Wecker
(74) *Attorney, Agent, or Firm* — Greenblum & Bernstein, P.L.C.

(57) ABSTRACT

A blood test apparatus negatively pressurizes a vicinity of a site to be punctured for collecting blood at an appropriate time without resorting to a special operation. More specifically, a blood test apparatus includes a housing having an opening; a puncturer; a first sensor that detects contact of a front face of the opening with a site to be punctured; a negative pressure generator that negatively pressurizes an inside of the opening; and a blood sensor that collects blood. The negative pressure generator starts when the first sensor detects the contact of the front face of the opening with the site to be punctured.

19 Claims, 14 Drawing Sheets

BLOOD TEST APPARATUS AND BLOOD TEST METHOD

TECHNICAL FIELD

The present invention relates to a blood test apparatus and a blood test method.

BACKGROUND ART

Conventionally, as an apparatus for measuring the blood sugar level, an apparatus combining a puncturing device for making a scar on a fingertip and a measuring device attached with a disposable blood sensor for sampling a small amount of blood squeezed from the fingertip where the scar is made, is widely used.

However, if such a puncturing device and a measuring device are provided separately, the patient needs to puncture the skin with the puncturing device and then sample blood using the measuring device, which makes the measuring operation complex.

Therefore, a blood test apparatus that integrates a lancet with a puncturing needle and a measuring device to which a blood sensor is attached, is proposed (see Patent Document 1). As shown in FIG. 13, proposed blood test apparatus 1 has cylinder-shaped housing 2, plunger 3 that moves back and forth inside housing 2, lancet 4 that has one end 4a held by plunger 3 and the other end 4b attached with blood collection needle 5, and blood sensor 6 attached to one end 2a of housing 2.

Test steps using blood test apparatus 1 will be described. First, blood sensor 6 is made to abut on skin 7, which is the part to be punctured, of the patient. Next, latch convex part 9a of handle 9 connected to plunger 3 and latch concave part 2b formed on housing 2 are disengaged. Plunger 3 urged by spring 10 is thereby propelled in the direction of arrow 8. In response to this, lancet 4 held by plunger 3 and blood collection needle 5 attached to this lancet 4 are also propelled in the direction of arrow 8.

Propelled needle 5 goes through blood sensor 6 and makes a tiny scar on skin 7. The blood flowing out from this scar is detected by a detecting section of blood sensor 6. A signal obtained according to the glucose in blood is led to measuring circuit 12 from connecting terminal 6a via connector 11. Measuring circuit 12 calculates the blood sugar level of the sampled blood and displays the calculation result on display section 13.

Patent Document 1: Japanese Patent Application Publication No. 2003-524496

DISCLOSURE OF INVENTION

Problems to be Solved by the Invention

In the test using the blood test apparatus, the blood flowing out from the skin punctured with blood collection needle 5 is preferably sampled more easily into blood sensor 6, and preferably flows out from the skin immediately after puncturing. Therefore, a vacuum pump may be provided in the blood test apparatus to create a negative pressure around the part to be punctured on which blood sensor 6 abuts.

However, when blood is tested using the blood test apparatus provided with a vacuum pump and the like, the patient holds the apparatus with one hand, presses blood sensor 6 against the skin, operates the switch for driving the vacuum pump, and performs the operation for releasing handle 9 to propel lancet 4. Therefore, the apparatus is difficult to be hold stably and is likely to miss from the part of the skin to be tested, which may make adequate measurement difficult.

Means for Solving the Problem

The blood test apparatus of the present invention has: a housing with an opening part; a puncturing section that is arranged inside the opening part; a first sensing section that detects a contact between a part to be punctured and a front surface of the opening part; a negative pressure section that creates a negative pressure inside the opening part; a blood sensor that samples blood flowing out from the part punctured with the puncturing section; and a measuring circuit that measures a signal obtained from the blood sensor that analyzes components in the blood. Further, the negative pressure section in the blood test apparatus of the present invention starts when the first sensing section detects a contact between the part to be punctured and the front surface of the opening part

Advantageous Effect of the Invention

According to the blood test apparatus of the present invention, by pressing the blood sensor against the part to be punctured, a negative pressure means can start automatically. Therefore, in the blood test, the negative pressure means can start even if the patient does not perform special operation.

Further, by puncturing the skin plumped up by the negative pressure created by the negative pressure means around the part to be punctured, it is possible to sample blood in a simple manner and perform test reliably.

Further, the negative pressure means starts after the part to be punctured is detected, so that it is not necessary to drive the negative pressure means before the part to be punctured is made to abut on the blood sensor. Therefore, battery life can be extended by reducing power consumption for driving the negative pressure means, so that it is possible to realize a blood test apparatus that particularly excels in portability.

BEST MODE FOR CARRYING OUT THE INVENTION

Figure 1:
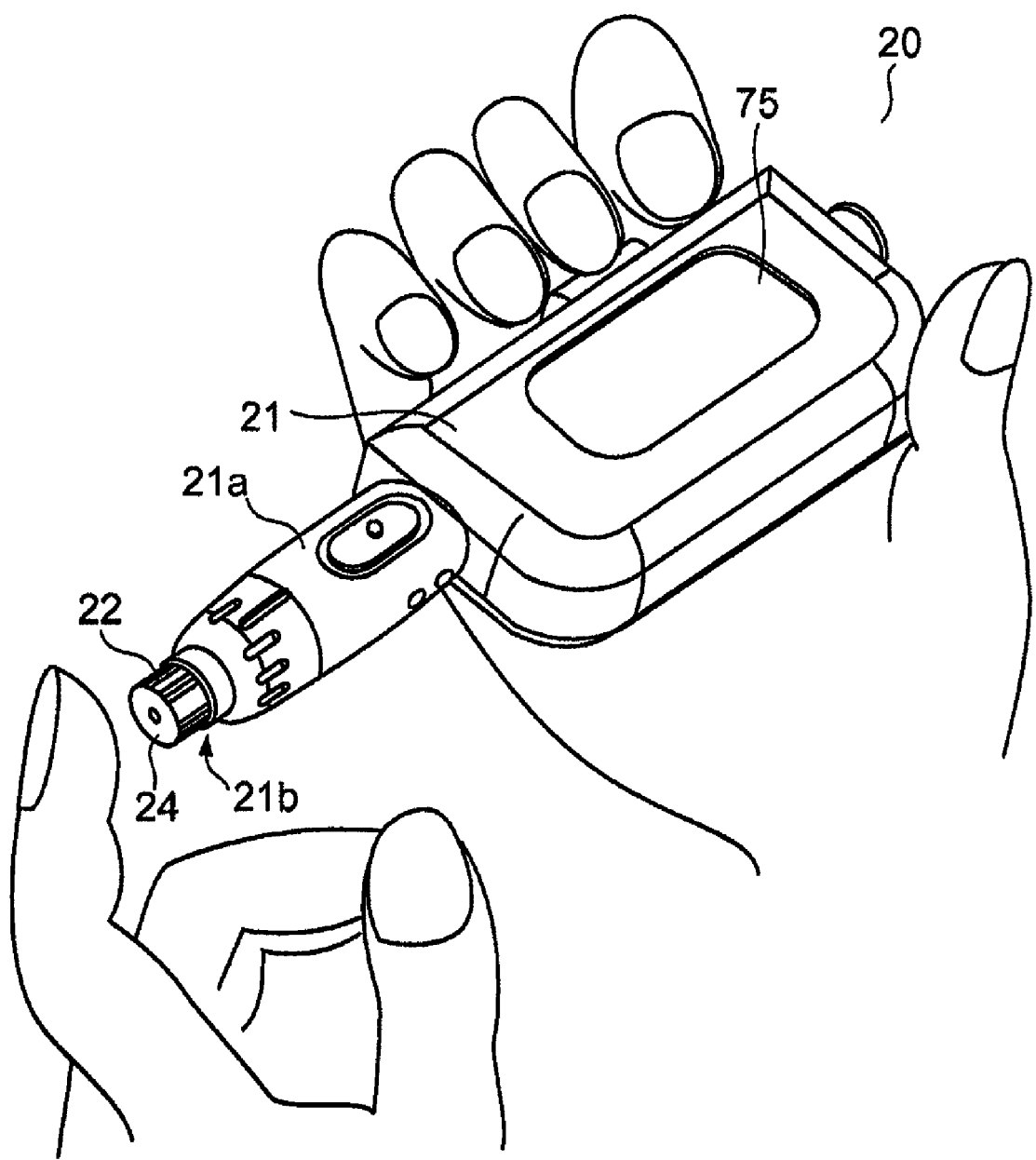
FIG. 1 is a diagrammatic perspective view of a blood test apparatus in use.

FIG. 1 shows an appearance of one example of the blood test apparatus. That is, FIG. 1 shows a state where the patient holds blood test apparatus 20 with the right hand and tries to sample blood from the index finger of the left hand. In FIG. 1, cylinder body 21a is formed on one side of housing 21. Blood sampling cartridge 22 with blood sensor 24 is attached to opening part 21b of cylinder body 21a. Housing 21 also has display section 75.

Figure 2:
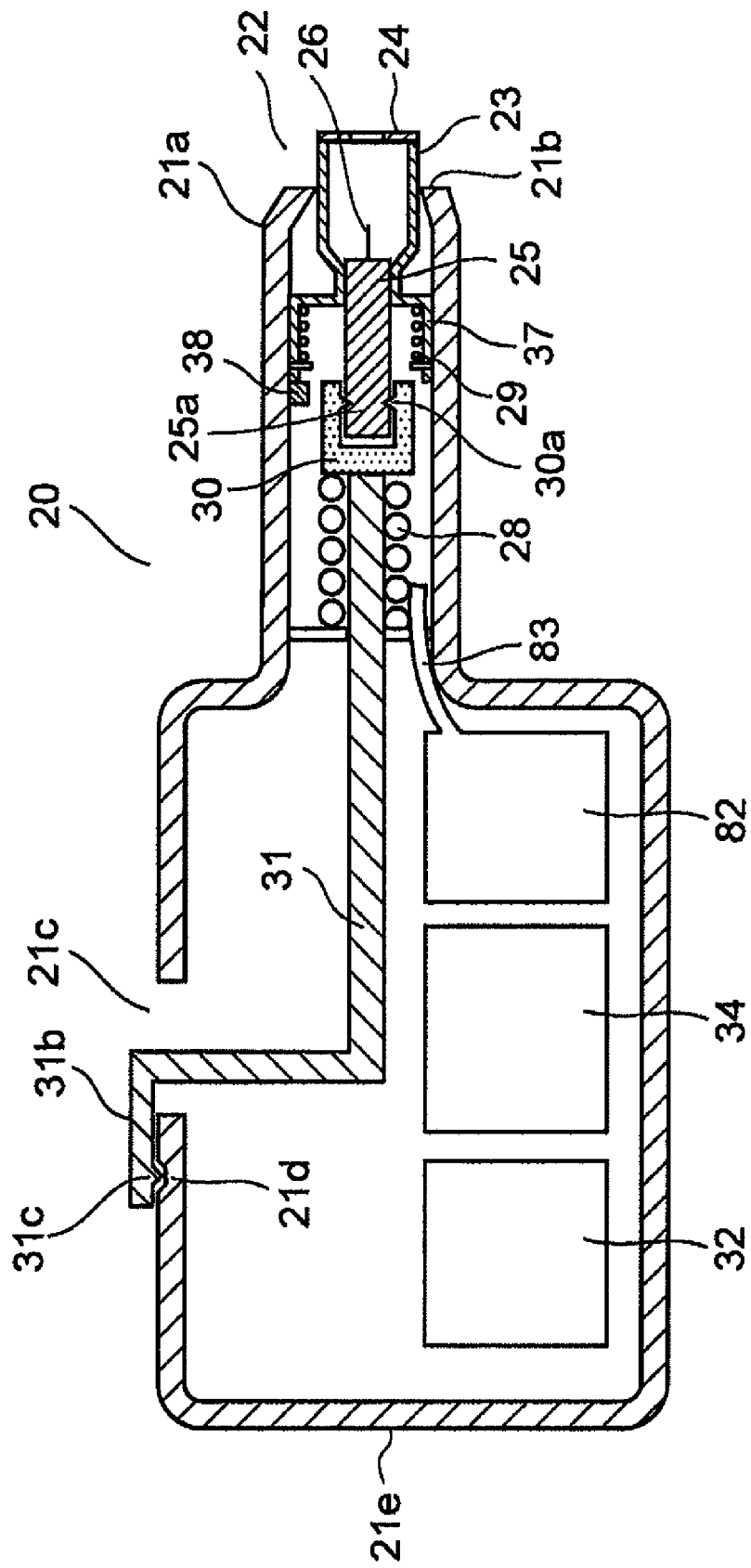
FIG. 2 is a cross-sectional view of the blood test apparatus.

FIG. 2 is a cross-sectional view of one example of the blood test apparatus. As described above, blood test apparatus 20 has housing 21 formed with resin. On one side of housing 21, cylinder body 21a (for example, having the shape of a cylinder) with opening part 21b is formed. Blood sampling cartridge 22 is attached to opening part 21b of cylinder body 21a.

Blood sampling cartridge 22 has a puncturing means integrated with holder 23 (for example, having the shape of a cylinder) and blood sensor 24. Blood sensor 24 is attached to one end of holder 23. The puncturing means include lancet 25 that is provided slidably inside holder 23, and blood collection needle 26 that is attached to the other end of lancet 25.

Although described in detail later, blood sensor 24 includes electrode system including a plurality of electrodes and connecting terminals connected to the electrode system, and connectors provided in the blood test apparatus contact with the connecting terminals.

Grip part 25a formed at the other end of lancet 25 configuring blood sampling cartridge 22 is held by holding part 30a provided at one end of plunger 30 that slides in cylinder body 21a. Handle 31 is connected to plunger 30. Latch convex part 31c is formed at one end 31b of handle 31. Handle 31 goes through hole 21c formed in housing 21 and is latched by the joint of latch convex part 31c and latch concave part 21d.

Puncturing spring 28 urges plunger 30 and lancet 25 included in blood sampling cartridge 22 attached to plunger 30 in the direction of the needle tip. Holder pressing spring 29 urges holder 23 and blood sensor 24 attached to holder 23 out of blood sampling cartridge 22 attached to cylinder body 21a, in the direction of the needle tip. Slider 37 holds holder pressing spring 29 and slides inside cylinder body 21a.

The blood test apparatus of the present invention has the first sensing means that detects that the part to be punctured is located in an appropriate position. Here, the "appropriate position" means an opening part of the housing in which the puncturing means is arranged. The first sensing means in FIG. 2 is mechanical switch 38 provided inside cylinder body 21a. When holder 23 moves in a direction to be immersed in cylinder body 21a, mechanical switch 38 is pressed by slider 37. Therefore, mechanical switch 38, which is the first sensing means, is not driven unless blood sampling cartridge 22 is attached.

Further, measuring circuit 32 is housed at the side of one side 21e of housing 21. Measuring circuit 32 connects with connectors (described later) formed in cylinder body 21a. Further, battery 34 that supplies power to measuring circuit 32 is also arranged in the blood test apparatus of the present invention.

The blood test apparatus of the present invention has a negative pressure means. The negative pressure means of the blood test apparatus in FIG. 2 is vacuum pump 82. The output of negative pressure means 82 is connected to inside cylinder body 21a via negative pressure path 83. Therefore, negative pressure means 82 can create a negative pressure in cylinder body 21a and holder 23 of blood sampling cartridge 22.

FIG. 3 is an exploded cross-sectional view showing blood sampling cartridge 22, and the periphery of opening part 21b of cylinder body 21a to which blood sampling cartridge 22 is attached.

Figure 3A:
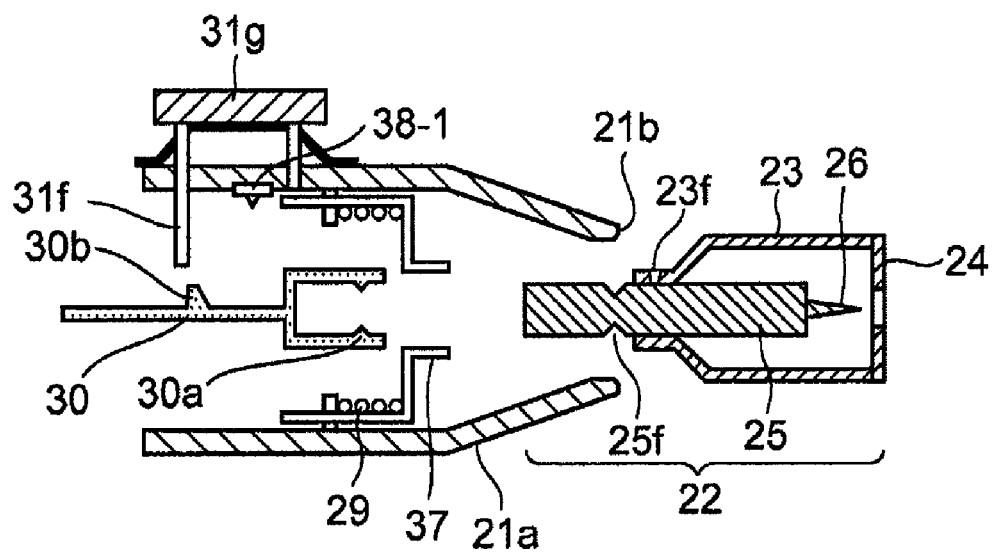
FIG. 3A is a cross-sectional view showing the main part before a blood sampling cartridge is attached to an attaching part of the blood test apparatus.

FIG. 3A shows a state before blood sampling cartridge 22 is attached to opening part 21b of cylinder body 21a. Holder 23 and lancet 25 of blood sampling cartridge 22 are fixed to each other with fixing claw 23f. Grip part 25f is formed in lancet 25.

On the other hand, in cylinder body 21a, plunger 30 is provided to be slidable in front and back directions (in this figure, in right and left directions). Plunger 30 has holding part 30a that holds grip part 25f of lancet 25. Further, plunger 30 has projecting part 30b and is fixed by the joint of projecting part 30b and plunger fixing member 31f provided in cylinder body 21a. Plunger fixing member 31f interlocks with button 31g. When button 31g is pressed, plunger fixing member 31f engages with projecting part 30b provided in plunger 30 and fixes plunger 30.

Further, slider 37 is provided in cylinder body 21a to be slidable in front and back directions (in this figure, in right and left directions). Slider 37 is urged by holder pressing spring 29 toward opening part 21b. Mechanical switch 38-1 provided inside cylinder body 21a is pressed by slider 37 which has moved toward inside cylinder body 21a. As described later, mechanical switch 38-1 detects that the part to be punctured is located in an appropriate position. Positioning the part to be punctured in an appropriate position includes, for example, positioning the part to be punctured so as to contact with opening part 21b.

Figure 3B:
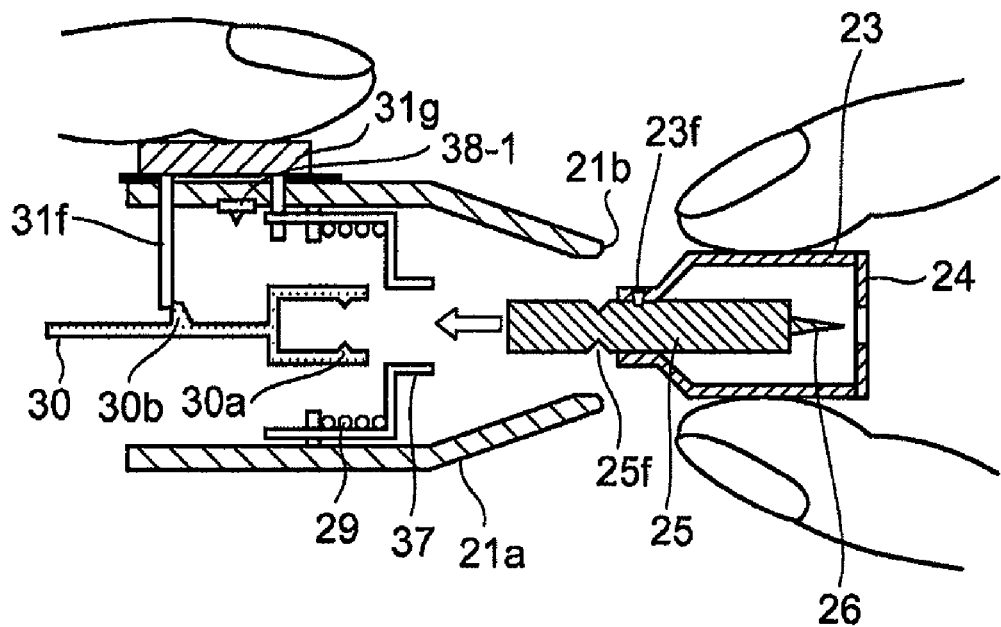
FIG. 3B is a cross-sectional view showing the main part when the blood sampling cartridge is being attached to the attaching part of the blood test apparatus.

FIG. 3B shows a state where blood sampling cartridge 22 is attached to cylinder body 21a from opening part 21b. When blood sampling cartridge 22 is inserted into cylinder body 21a in the direction of the arrow, button 31g is pressed, and thereby plunger 30 is fixed with plunger fixing member 31f.

Figure 3C:
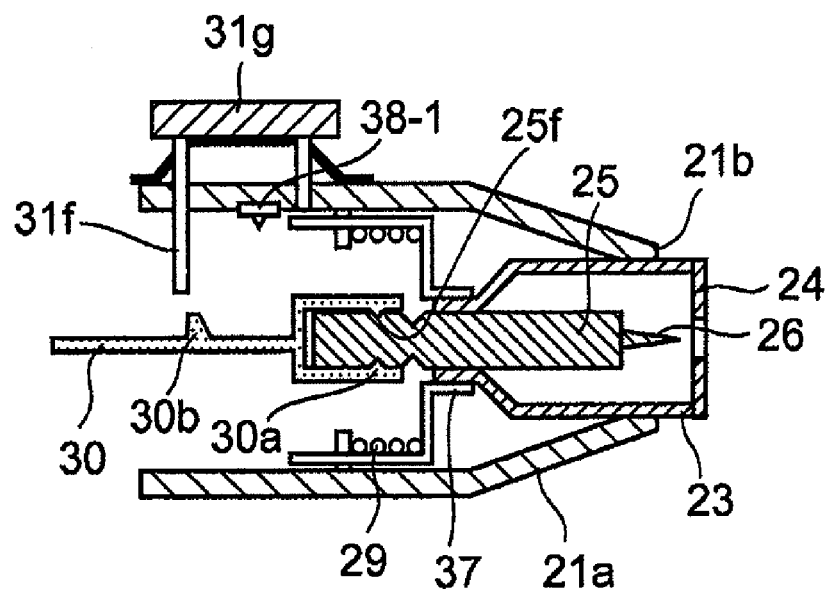
FIG. 3C is a cross-sectional view showing the main part when the blood sampling cartridge is attached to the attaching part of the blood test apparatus.

FIG. 3C shows a state where blood sampling cartridge 22 is attached to opening part 21*b* of cylinder body 21*a* of the blood test apparatus. Holding part 30*a* of plunger 30 holds grip part 25*f* of lancet 25 configuring blood sampling cartridge 22. Further, in blood sampling cartridge 22, holder 23 engages with slider 37 attached in cylinder body 21*a*. Blood sensor 24 of attached blood sampling cartridge 22 is arranged in a state blood sensor 24 projects through opening part 21*b* of cylinder body 21*a*. Blood sensor 24 can be pushed back into opening part 21*b* against the urging force of holder pressing spring 29.

Blood sensor 24 of blood sampling cartridge 22 attached to cylinder body 21*a* and the puncturing means (including lancet 25 and blood collection needle 26) can operate separately. That is, lancet 25 of blood sampling cartridge 22 is driven by plunger 30. On the other hand, apart from lancet 25, holder 23 and blood sensor 24 interlock with slider 37 and can move in and out of housing 21 through opening part 21*b* of cylinder 21*a*.

Further, the fixing of fixing claw 23*f* (which fixes lancet 25) in blood sampling cartridge 22 is preferably released when blood sampling cartridge 22 is attached to cylinder body 21*a*. For example, as shown in FIG. 3G and FIG. 3H, it is only necessary to form supporting part 23*g*, which is the center of rotation of fixing claw 23*f* (and which may be formed by resin molding). FIG. 3G shows a state before the fixing of fixing claw 23*f* and lancet 25 is released, and FIG. 3H shows a state after the fixing is released. When holder 23 of blood sampling cartridge 22 engages with slider 37, an end of slider 37 presses fixing claw 23*f* so that fixing claw 23*f* rotates (moves like a seesaw) using supporting part 23*g* as a supporting point. By this rotation, fixing claw 23*f* is released from lacking part 25*g* in lancet 25, and thereby the fixing is released.

Figure 3D:
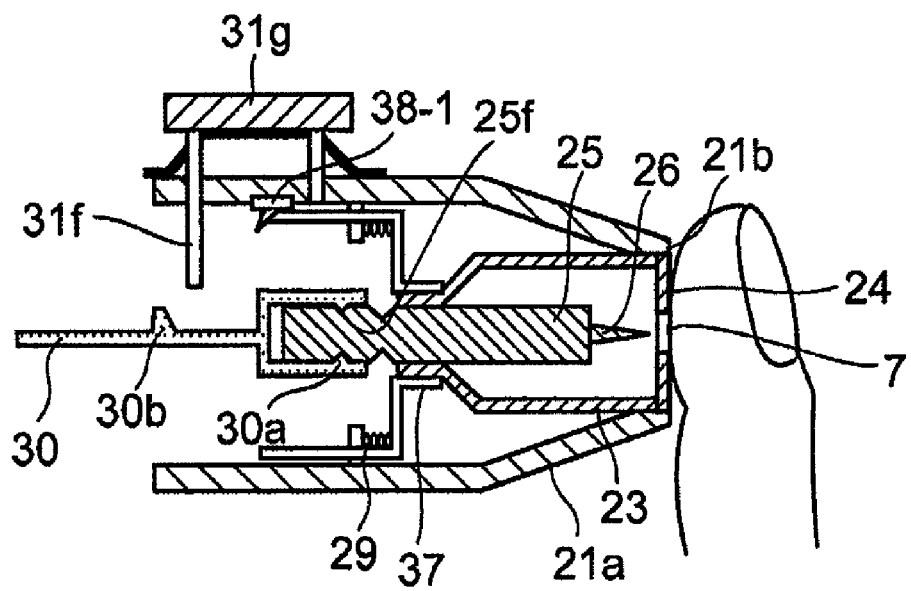
FIG. 3D is a cross-sectional view showing the main part when a blood sensor of the blood sampling cartridge attached to the attaching part of the blood test apparatus is forced into the blood test apparatus by the part to be punctured.

FIG. 3D shows a state where the patient performing a blood test puts skin 7 of the part to be punctured (for example, the fingertip) to blood sensor 24 at the tip of blood sampling cartridge 22 and forces blood sensor 24 into opening part 21*b* of cylinder body 21*a*. That is, holder 23 and blood sensor 24 move toward inside cylinder body 21*a* by resisting the urging force of holder pressing spring 29, and stay when blood sensor 24 matches opening part 21*b* of cylinder body 21*a*. As a result, skin 7 of the part to be punctured contacts with opening part 21*b* of cylinder body 21*a*, and opening part 21*b* is covered. In the state shown in FIG. 3D, mechanical switch 38-1, which is the first sensing means, is pressed to the first position by slider 37 which has moved.

Figure 3E:
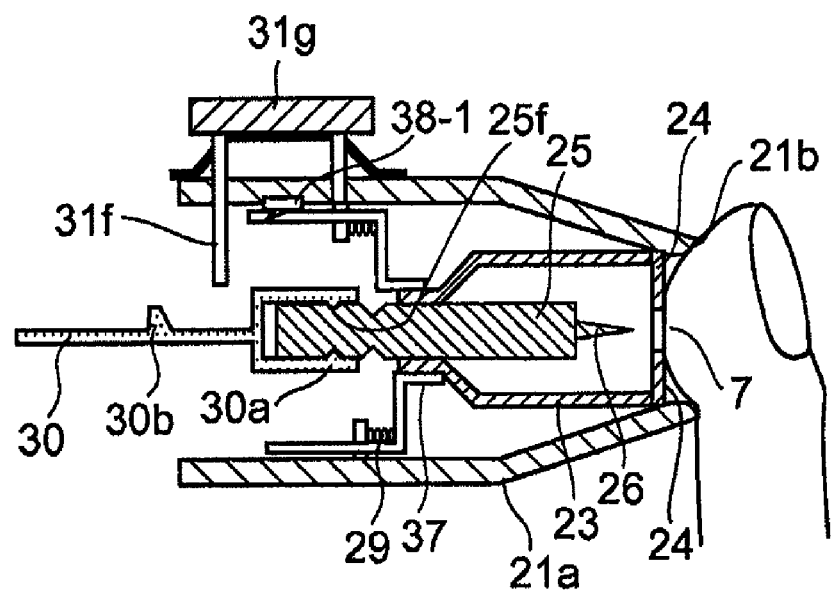
FIG. 3E is a cross-sectional view showing the main part when the blood sensor of the blood sampling cartridge attached to the attaching part of the blood test apparatus is forced into the blood test apparatus by the part to be punctured plumped up by a negative pressure.

When mechanical switch 38-1 is pressed to the first position, negative pressure means 82 starts and creates a negative pressure inside cylinder body 21*a*. Negative pressure means 82 preferably starts automatically. FIG. 3E shows a state where skin 7 of the part to be punctured is sucked in and plumped up in cylinder body 21*a* to which a negative pressure is created by negative pressure means 82. By plumped skin 7 of the part to be punctured, blood sensor 24 moves further toward inside cylinder body 21*a*. In the state shown in FIG. 3E, mechanical switch 38-1, which is the first sensing means, is pressed to a second position by slider 37 which has further moved. That is, mechanical switch 38-1 also functions as the second sensing means that detects a change in the shape of the part to be punctured by a negative pressure, i.e., detects a plumpness of the part to be punctured. Further, the second sensing means may be a different member from mechanical switch 38-1. For example, a mechanical switch provided separately further behind (in the left in the figure) mechanical switch 38-1 in cylinder body 21*a*, may be used as the second sensing means.

After mechanical switch 38-1 is pressed to the second position by slider 37, the part to be punctured is punctured. Therefore, display section 75 preferably displays that mechanical switch 38-1 is pressed to the second position to encourage the patient to perform puncturing manually using a puncturing button and the like, or the apparatus preferably performs puncturing automatically after mechanical switch 38-1 moves to the second position.

Figure 3F:
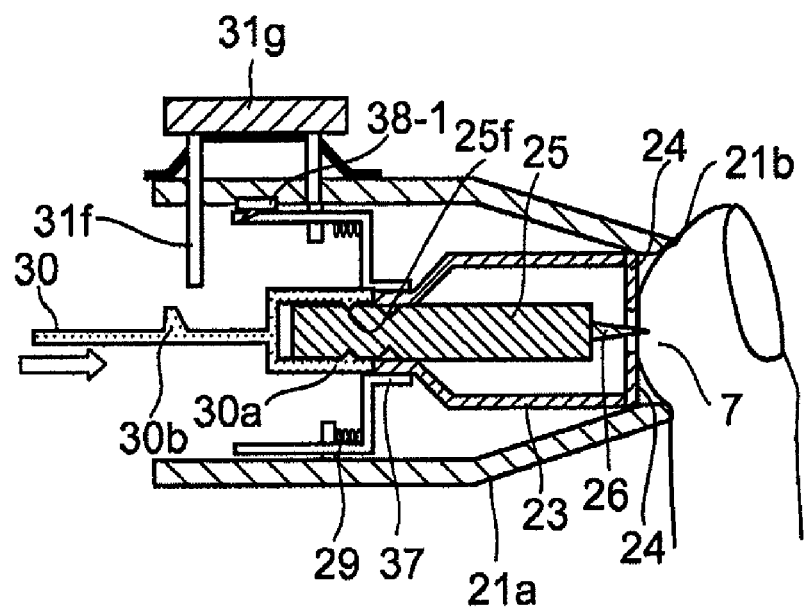
FIG. 3F is a cross-sectional view showing the main part when the part to be punctured that is abut on the blood sensor of the blood sampling cartridge attached to the attaching part of the blood test apparatus, is punctured.
Figure 3G:
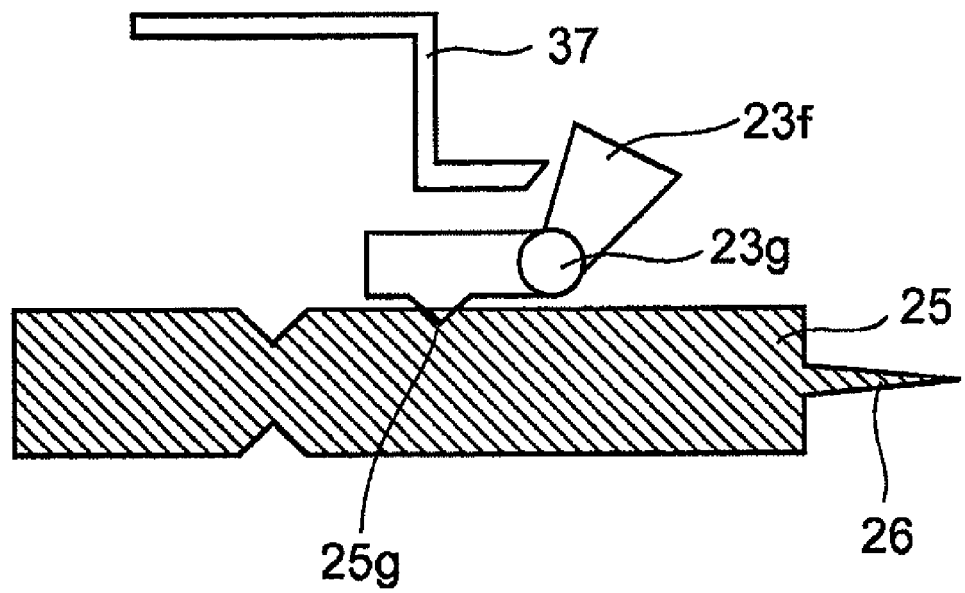
FIG. 3G illustrates a state where the fixing of the lancet fixed by a fixing claw of the blood sampling cartridge is released, and is a cross-sectional view showing a state before the fixing is released.
Figure 3H:
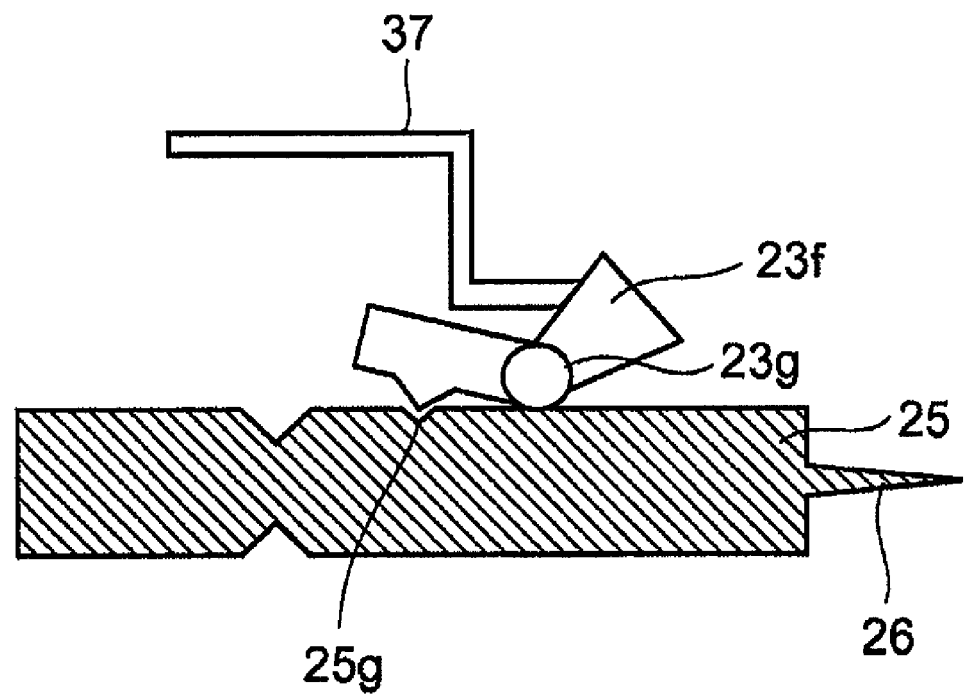
FIG. 3H illustrates a state where the fixing of the lancet fixed by the fixing claw of the blood sampling cartridge is released, and is a cross-sectional view showing a state after the fixing is disengaged.

FIG. 3F shows a state where skin 7 of the part to be punctured is punctured. Plunger 30 moves toward the needle tip, and blood collection needle 26 projects from blood sensor 24 and punctures skin 7. In this way, plunger 30 can move separately from holder 23.

After puncturing, plunger 30 is pulled backward and enters the state shown in FIG. 3E, and blood is sampled from the skin of the patient and flows into blood sensor 24. As described later, by providing in blood sensor 24, a one electrode of the electrode system, which serves as a detecting electrode, it is possible to detect the inflow of blood. The inflow of blood is preferably displayed on display section 75, or the negative pressure means preferably stops automatically after detection.

Mechanical switch 38-1 in FIG. 3 may be an electrical switch or an optical switch. That is, when skin 7 of the part to be punctured forces blood sensor 24 into opening part 21*b* and thereby slider 37 moves, capacitance, electrical resistance, frequency, and the like, are changed and these changes are detected using an electrical switch, or the light transmission rate is changed and the change is detected using an optical switch (such as a photo interrupter).

An electrical switch utilizing electrical resistance (an electrical switch of an electrical resistance type) is arranged inside cylinder body 21*a* in the same way as mechanical switch 38-1 shown in FIG. 3. Blood sensor 24 is pressed by part 7 to be punctured and moves toward inside cylinder body 21*a* (leftward in FIG. 3). In response to this, slider 37 formed with conductive material moves to the position of the electrical switch of electrical resistance type and contacts with the electrical switch. The skin is detected based on the electrical resistance which changes by the contact.

The position where an electrical switch utilizing capacitance (an electrical switch of a capacitance type) is arranged is the same as that of the electrical switch utilizing the electrical conductivity. The electrical switch of the capacitance type has a pair of terminals and detects the skin based on an electrical change between the terminals (in this case, a change in capacitance). That is, blood sensor 24 is pressed by part 7 to be punctured and moves toward inside cylinder body 21*a*. In response to this, slider 37 formed with conductive material moves toward inside cylinder body 21*a* and contacts with the electrical switch of the capacitance type. When slider 37 contacts with both terminals of the pair of the electrical switch, the capacitance between the terminals in a pair changes. The skin is detected based on this change in capacitance.

The position where an electrical switch utilizing a frequency change (an electrical switch of a frequency change type) is arranged is the same as that of mechanical switch 38-1 shown in FIG. 3. The electrical switch of the frequency change type incorporates a coil. When slider 37 formed with conductive material approaches the coil to which a voltage is applied, the resonant frequency changes by a change in the distance between slider 37 and the coil according to a change in the inductance. The skin is detected based on this change in frequency.

The position where the photo interrupter optical switch is arranged is the same as that of mechanical switch 38-1 shown in FIG. 3. The reflective type photo interrupter optical switch detects the skin by blocking light. That is, blood sensor 24 is pressed by part 7 to be punctured and moves toward inside cylinder body 21a. In response to this, slider 37 formed with conductive material moves toward inside cylinder body 21a and blocks the light of the light emitting element of the photo interrupter optical switch. By the blocking of light, the input of the light receiving element of the photo interrupter optical switch changes. The skin is detected based on a change in input of the light receiving element.

[The Blood Sampling Cartridge]

Blood test apparatus 20 shown in FIG. 2 has blood sampling cartridge 22 that incorporates and integrates lancet 25 to which blood collection needle 26 is attached and blood sensor 24. All the members included in blood sampling cartridge 22 can be attached to and removed from cylinder body 21a together. Therefore, blood sensor 24 and blood collection needle 26 can be attached and replaced in a simple manner.

Further, when blood sampling cartridge 22 is attached, blood collection needle 26 is accommodated in holder 23, so that blood sampling cartridge 22 can be replaced securely without hurting the patient with blood collection needle 26 by error. Further, blood collection needle 26 is accommodated in holder 23, and so the patient does not feel fear. Furthermore, blood collection needle 26 does not allow direct touch and so is sanitary. Further, blood sensor 24 and blood collection needle 26 are replaced together every test, so that there is no fear that needle 26 is used several times and there is no threat of infection.

Figure 4:
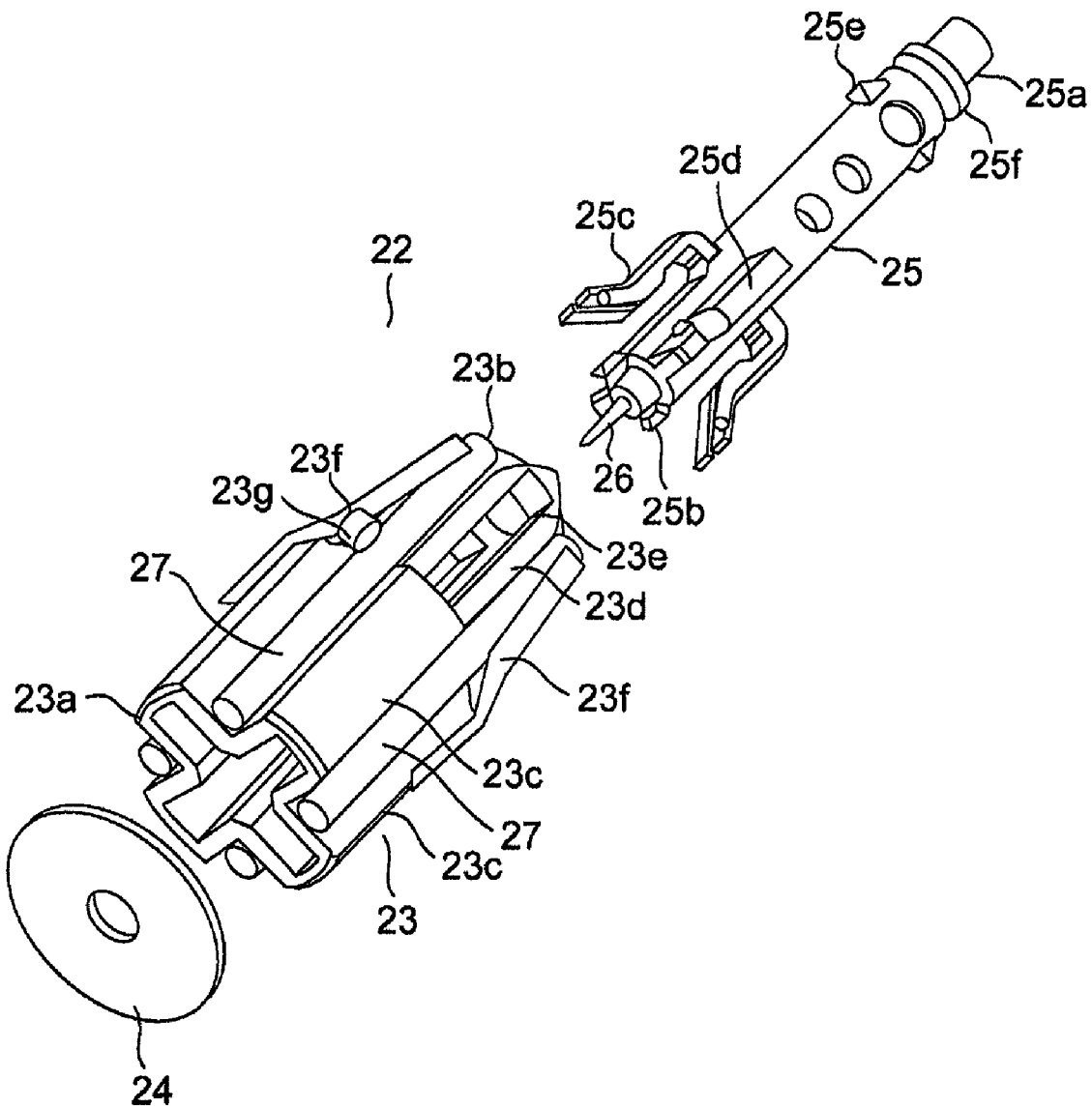
FIG. 4 is an assembly drawing of the blood sampling cartridge.

FIG. 4 is a diagrammatic perspective assembly view of an example of the blood sampling cartridge. In FIG. 4, blood sensor 24 that examines sampled blood is attached to one end 23a of holder 23. The outer surface of holder 23 has the shape of a cross, and connectors 27 formed with conductive metal (in the blood test apparatus) are led between cross-shaped convex parts 23c. The shape of the outer surface of holder 23 is not particularly limited and may be a regular polygon.

The other end of holder 23 has convex parts 23d formed integrated with convex parts 23c, and convex parts 23d have holes 23e.

Lancet 25 is inserted into holder 23. Guides 25c for preventing reuse, which are arranged 180 degrees apart from each other, are formed integrated with lancet 25. Further, guides 25d for improving linear mobility are provided between guides 25c 180 degrees apart from each other and slide inside holes 23e provided in convex parts 23d of holder 23. Grip part 25f is provided between convex parts 25e provided near one end 25a of lancet 25 and one end 25a.

Further, fixing claw 23f that fixes lancet 25 inserted into holder 23, is provided. Fixing claw 23f can rotate with respect to holder 23 and has supporting part 23g for the rotation. Fixing claw 23f is a resin elastic member that performs seesaw operation and releases the fixing of lancet 25 after blood sampling cartridge 22 is attached to cylinder body 21a (described above).

Figure 5A:
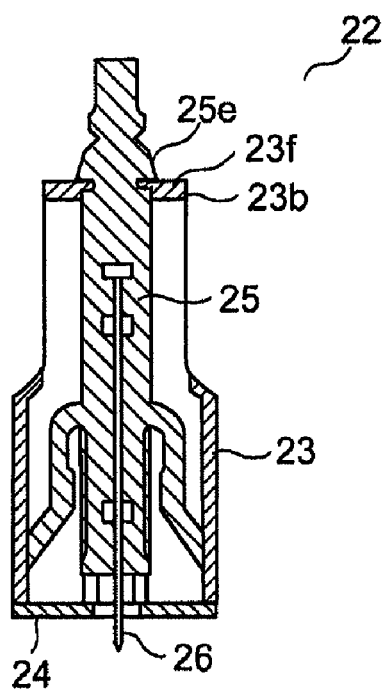
FIG. 5A is a cross-sectional view of the blood sampling cartridge, and shows a state upon puncturing.
Figure 5B:
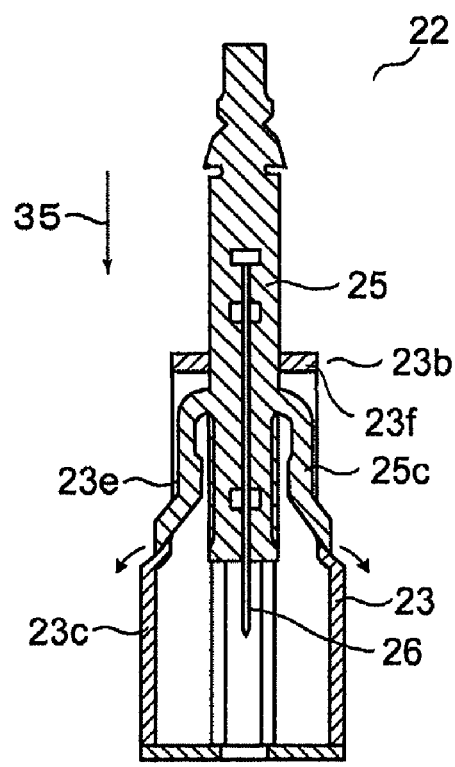
FIG. 5B is a cross-sectional view of the blood sampling cartridge, and shows a state after puncturing.

FIG. 5A is a cross-sectional view of blood sampling cartridge 22 upon puncturing, and FIG. 5B is a cross-sectional view of blood sampling cartridge 22 when puncturing is finished. In a state shown in FIG. 5A, blood collection needle 26 projects from blood sensor 24. Convex part 25e of lancet 25 is latched at latch part 23f provided at the other end 23b of holder 23, and so needle 26 does not project from blood sensor 24.

In FIG. 5B, blood collection needle 26 is accommodated in holder 23 and stays. The bases of guides 25c of lancet 25 are latched at latch part 23f provided at the other end 23b of holder 23 and stay. Therefore, lancet 25 does not fall off from holder 23.

In the state shown in FIG. 5B, blood sampling cartridge 22 is removed from cylinder body 21a. Even if lancet 25 is pushed in the direction of arrow 35, guides 25c run onto convex parts 23c from holes 23e of holder 23 by their elasticity. The bases of guides 25c are engaged at the ends of holes 23e and stay. Therefore, blood collection needle 26 does not project again from blood sensor 24 and is secure. Further, needle 26 does not project and so the patient does not feel fear.

Figure 6:
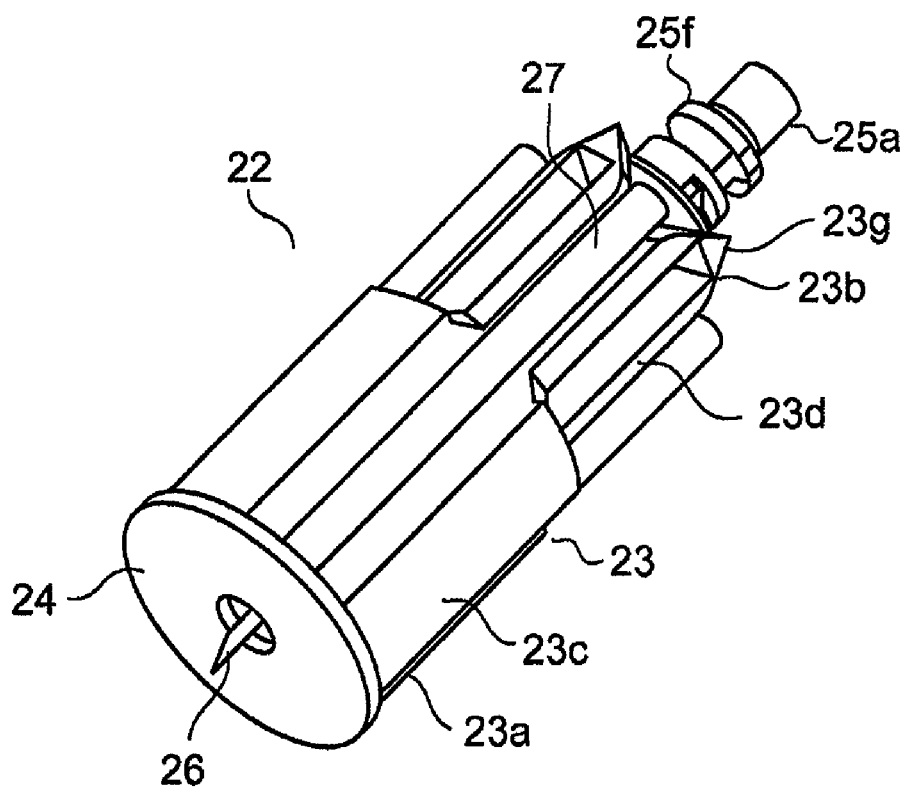
FIG. 6 is a diagrammatic perspective view of the blood sampling cartridge.

FIG. 6 is a diagrammatic perspective view of blood sampling cartridge 22. As shown in FIG. 6, the height of cross-shaped convex part 23c formed on the one end 23a side of holder 23 is higher than the height of cross-shaped convex part 23d formed on the other end 23b side of holder 23. That is, the convex part 23d side of holder 23 is thinner than the convex part 23c side. In this way, if the front part of blood sampling cartridge 22 with respect to the insertion direction is thinner than the rear part, blood sampling cartridge 22 can be inserted to cylinder body 21a in a simple manner. Further, tip part 23g (on the end 23b side) of convex part 23d on the other end 23b side projects at an acute angle. This is important to make sure that a connector (described later) formed on the cylinder body 21a side contacts with a desired position of the blood sensor.

The whole of blood sampling cartridge 22 can be attached to and removed from cylinder body 21a, and so needle 26 and blood sensor 24 can be freely attached to and removed from cylinder body 21a together. Therefore, blood sensor 24 and needle 26 can be attached and replaced in a simple manner.

Figure 7:
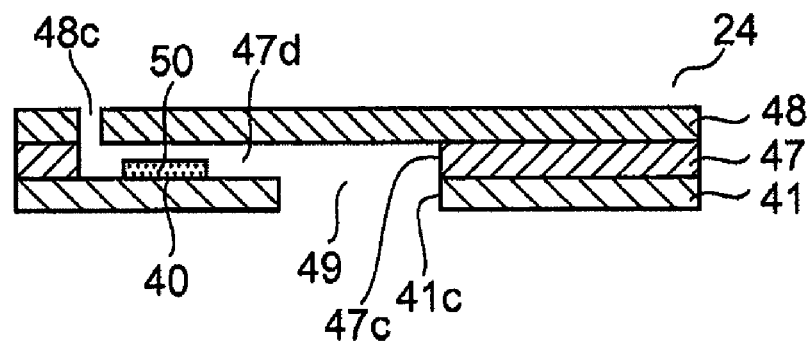
FIG. 7 is a cross-sectional view of the blood sensor.

FIG. 7 is a cross-sectional view of an example of the blood sensor in the blood test apparatus of the present invention. Blood sensor 24 has substrate 41, spacer 47 pasted on the upper surface of substrate 41, and cover 48 pasted on the upper surface of spacer 47. Hole 41c provided in substrate 41 and hole 47c provided in spacer 47 form blood storing part 49. Supply channel 47d is connected to storing part 49. The tip of supply channel 47d communicates with air hole 48c.

Detecting section 40 arranged in supply channel 47d includes electrode system as described later. The detecting section detects the inflow of blood and the blood components. Further, reagent 50 is placed on at least part of detecting section 40. Reagent 50 is, for example, prepared by dropping on detecting section 40 formed on substrate 41, a reagent solution prepared by adding and dissolving PQQ-GDH (0.1 to 5.0 U/blood sensor) potassium ferricyanide (10 to 200 mM), maltitol (1 to 50 mM) and taurine (20 to 200 mM) in a 0.01 to 2.0 wt % aqueous solution of CMC, and drying the reagent solution.

Figure 8A:
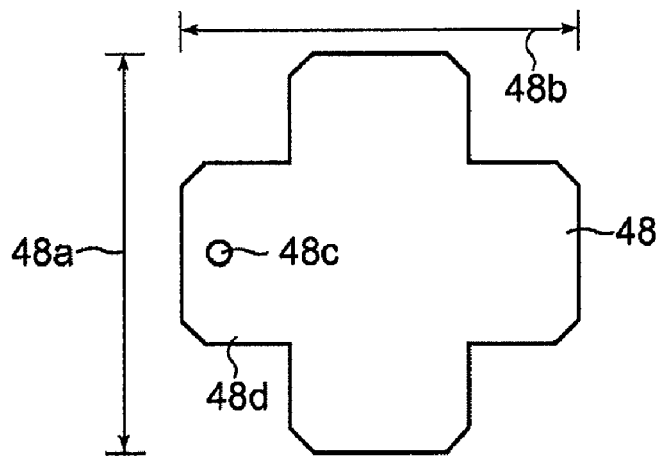
FIG. 8A is an exploded plan view of the blood sensor and shows a cover.
Figure 8B:
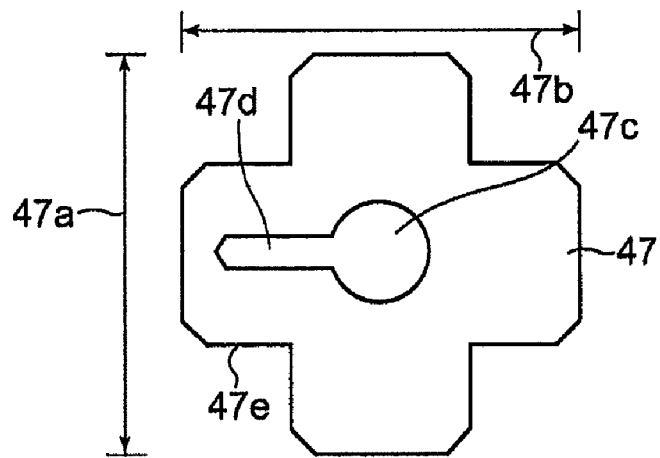
FIG. 8B is an exploded plan view of the blood sensor and shows a spacer.
Figure 8C:
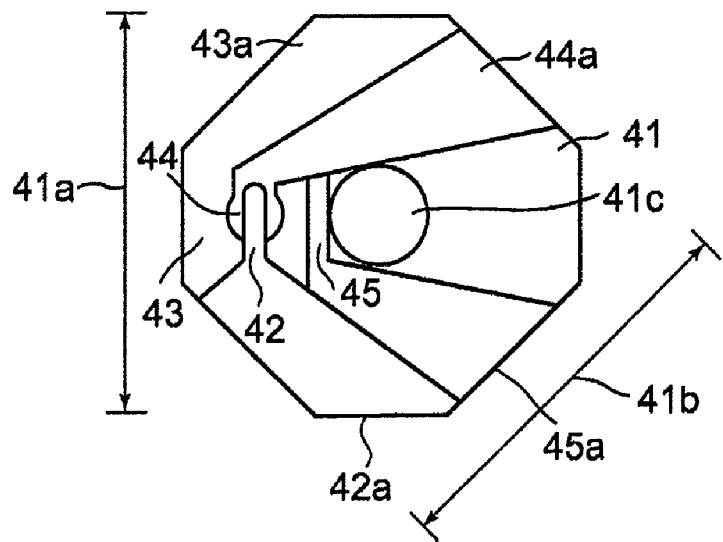
FIG. 8C is an exploded plan view of the blood sensor and shows a substrate.

FIG. 8 is an exploded plan view of blood sensor 24. Blood sensor 24 has cover 48 shown in FIG. 8A, spacer 47 shown in FIG. 8B and substrate 41 shown in FIG. 8C.

FIG. 8C is a plan view of substrate 41. Although substrate 41 is an octagon, the shape of the substrate is not particularly limited. The size may be adjusted as appropriate, and, for example, one dimension 41a is set 9 mm, and the other dimension 41b is set 8 mm. Material of substrate 41 is preferably resin such as polyethylene terephthalate (PET), and its thickness preferably falls in a range of 0.075 to 0.25 mm (preferably 0.188 mm).

On one surface of substrate 41 (the surface that is pasted with spacer 47), each electrode of electrode system 42 to 45 and connecting terminals 42a to 45a connected to each electrode of electrode system 42 to 45, respectively, are formed in an integrated manner. Each electrode of electrode system 42 to 45 and connecting terminals 42a to 45a can be formed by forming a conductive layer using the sputtering method or the vapor deposition method, using gold, platinum, palladium as materials and applying laser machining to this conductive layer. Hole 41c is provided in substrate 41, and its diameter may be approximately 2.0 mm. Hole 41c is preferably provided in approximately the center of substrate 41.

FIG. 8B is a plan view of spacer 47. Spacer 47 has the shape of an approximate cross, but may be a polygon (preferably a regular polygon). If the spacer has the shape of a cross, connectors (not shown) can be arranged in its dent easily. The size of spacer 47 may be adjusted according to the size of substrate 41, and, for example, one dimension 47a may be 9 mm, and the other dimension 47b may be 8 mm. The thickness of spacer 47 may fall in a range of 0.05 to 0.15 mm (preferably 0.1 mm).

Hole 47c is provided in spacer 47, and is in the position corresponding hole 41c which is provided in approximately the center of substrate 41. The diameter of hole 47c may be made the same (approximately 2.0 mm) as the diameter of hole 41c. Slit 47d is formed in the direction from hole 47c to cross-shaped first convex part 47e and corresponds the blood supply channel. Although the cavity of supply channel 47d may be set approximately 0.144 μL by setting the width of the groove of slit 47d 0.6 mm and setting the length in the flow channel direction 2.4 mm, the size may be adjusted as appropriate. In this way, test can be performed with a small amount of blood, so that the load on the patient becomes small, and the patient does not feel fear. The material of spacer 47 may be resin such as polyethylene terephthalate (PET).

FIG. 8A is a plan view of cover 48. The shape and size of cover 48 may be made the same as those of spacer 47. Air hole 48c is provided in cross-shaped first convex part 48d so as to correspond the tip part of supply channel 47d. Preferably, the diameter of air hole 48c is approximately 50 μm.

The material of cover 48 is plastic, and preferably polyethylene terephthalate. The thickness of cover 48 may fall in a range of 0.05 to 0.25 mm (preferably 0.075 mm). The reverse side of cover 48 corresponding to the ceiling part of supply channel 47d is preferably subjected to hydrophilicity treatment to make the blood sampled in storing part 49 smoothly flow in supply channel 47d by capillary action. Further, the reverse side of cover 48 corresponding to the ceiling part of hole 47c is preferably subjected to water-repellency treatment. Still further, the surface of cover 48 (the reverse side of the surface pasted with the spacer) is preferably subjected to water-repellency treatment.

Figure 9:
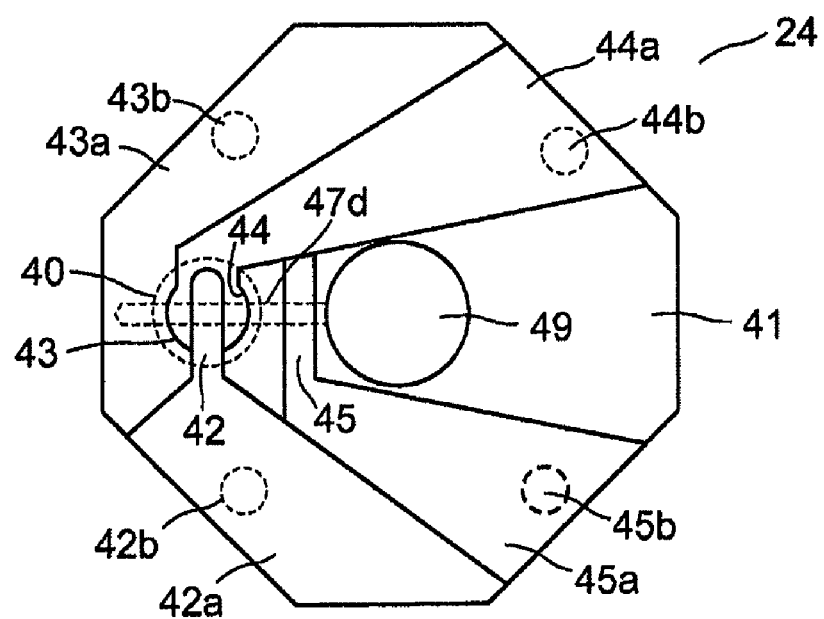
FIG. 9 is a perspective plan view of the blood sensor.

FIG. 9 is a perspective plan view of blood sensor 24. Each electrode of electrode system 42 to 45 are formed on substrate 41 and configure a detecting section. Each electrode of electrode system 42 to 45 function as, for example, a working electrode, a detecting electrode, a counter electrode and an Hct electrode, respectively. The "working electrode" refers to an electrode for measuring blood components, the "detecting electrode" refers to an electrode for sensing whether or not blood is supplied to the detecting section, the "counter electrode" refers to a counterpart electrode of the working electrode, and the "Hct electrode" refers to an electrode for measuring the hematocrit level in blood. Each electrode of electrode system 42 to 45 are connected to relevant connecting terminals 42a to 45a, respectively, and connecting terminals 42a to 45a are arranged along the outer periphery of substrate 41.

The reagent contacts with at least part of detecting section 40 on substrate 41. The reagent is preferably arranged in contact with one electrode 42 of the electrode system, which functions as a working electrode, and one electrode 44 of the electrode system, which functions as a counter electrode. On the other hand, the reagent is preferably not arranged in contact with one electrode 45 of the electrode system, which functions as an Hct electrode.

The blood flowing out from the skin punctured with blood collection needle 26 is guided into storing part 49. The blood guided into storing part 49 flows in supply channel 47d by capillary action, is led into detecting section 40, and reacts with regent 50 in detecting section 40. The result of the reaction is led to connecting terminals 42a, 43a, 44a and 45a connected to the electrode system.

Further, the result of the reaction is led to terminals (33a, 33b, 33c and 33d, not shown) formed at cylinder body 21a via connectors (27a, 27b, 27c and 27d, not shown) which contact with connecting terminals 42a, 43a, 44a and 45a, and, further, the result of the reaction is led to measuring circuit 32 from the terminals.

As shown in FIG. 9, connecting terminals 42a to 45a have contact parts 42b to 45b, respectively, to contact with the connectors. Contact parts 42b, 43b, 44b and 45b contact with connectors 27a, 27b, 27c and 27d, respectively. Contact parts 42b, 43b, 44b and 45b are preferably arranged around a specific point so as to surround the specific point and arranged at equiangular intervals centered on the specific point.

The "specific point" is preferably provided in storing part 49 (inside hole 41c) on the surface of the substrate, and, more preferably, near the center of storing part 49. Further, the "specific point" may be provided on the axis where puncturing needle 26 moves, on the surface of the substrate. Still further, the specific point is preferably provided near the center of the rotation about the axis of the insertion direction for attaching the blood sampling cartridge to the attaching part, of the blood sampling cartridge. Further, contact parts 42b to 45b are preferably arranged at approximately the same distance from the specific point.

In this way, connectors 27 of the blood test apparatus contact with blood sensor 24 at equiangular intervals centered on the specific point, so that the connectors and the blood sensor can be connected adequately regardless of the angle at which the blood sampling cartridge is attached. Therefore, the blood sampling cartridge can be attached more easily.

If contact parts 42b, 43b, 44b and 45b are arranged at equiangular intervals centered on the specific point, when blood sampling cartridge 22 is attached to cylinder body 21a and the contact parts contact with the connectors, all the contact parts can contact with one of the connectors even if the rotation angle with respect to the axis of the insertion direction of the blood sampling cartridge is arbitrary. On the other hand, it is not clear which connectors contact with which contact parts. Therefore, to insert the blood sampling cartridge casually regardless of the rotation angle with respect to the axis of the insertion direction, a "reference terminal" is preferably provided for specifying which contact parts of the connecting terminals contact with which connectors.

Figure 10:
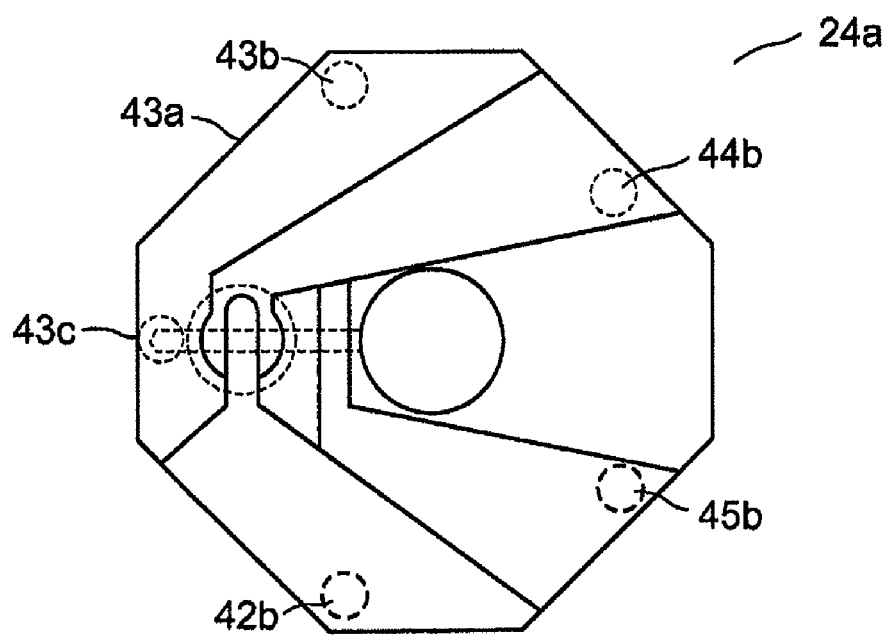
FIG. 10 is a perspective plan view of another example of the blood sensor.

FIG. 10 shows an example where blood sensor 24 has a reference terminal. Blood sensor 24a shown in FIG. 10 has the "reference terminal" for specifying the positions of the connecting terminals, in one of the connecting terminals, in addition to connecting terminals 42a to 45a. Blood sensor 24a may be the same as blood sensor 24 shown in FIG. 9 except that the reference terminal is provided. The reference terminal shown in FIG. 10 is reference contact part 43c, which is the position that contacts with the connector. Reference contact part 43c is provided in connecting terminal 43a together with contact part 43b, that is, contact part 43b and reference contact part 43c are connected via a conductor. Therefore, the resistance between contact part 43b and reference contact part 43c is zero. Reference contact part 43c may be provided in one of connecting terminals 42a to 45a and is not limited to connecting terminal 43a.

Contact parts 42b to 45b and reference contact part 43c are preferably provided near the outer periphery of blood sensor 24a, arranged around the specific point and arranged at equiangular intervals centered on the specific point. Therefore, five connectors 27 of cylinder body 21a are provided at equiangular intervals centered on the specific point so as to correspond contact parts 42b to 45b and reference contact part 43c, respectively. Preferably, blood sampling cartridge holder 23 including blood sensor 24a does not have the cross shape shown in FIG. 2, but has a star shape or the shape of a pentagon. Connectors 27 arranged in the attaching part of the test apparatus are arranged at the same angle around the star-shaped or pentagon-shaped holder.

By providing reference contact part 43c in addition to contact parts 42a to 45b, even if blood sampling cartridge 22 is inserted into cylinder body 21a at an arbitrary rotation angle with respect to the axis of the insertion direction, (A) one of the connectors can contact with one of the contact parts or the reference contact part, and (B) measuring circuit 32 can detect neighboring electrodes where the electrical resistance is zero, specify connecting terminals including the reference contact part, specify the positions of connecting terminals 42a to 45a, and further specify the functions of the electrode system connected to the connecting terminals.

Figure 11:
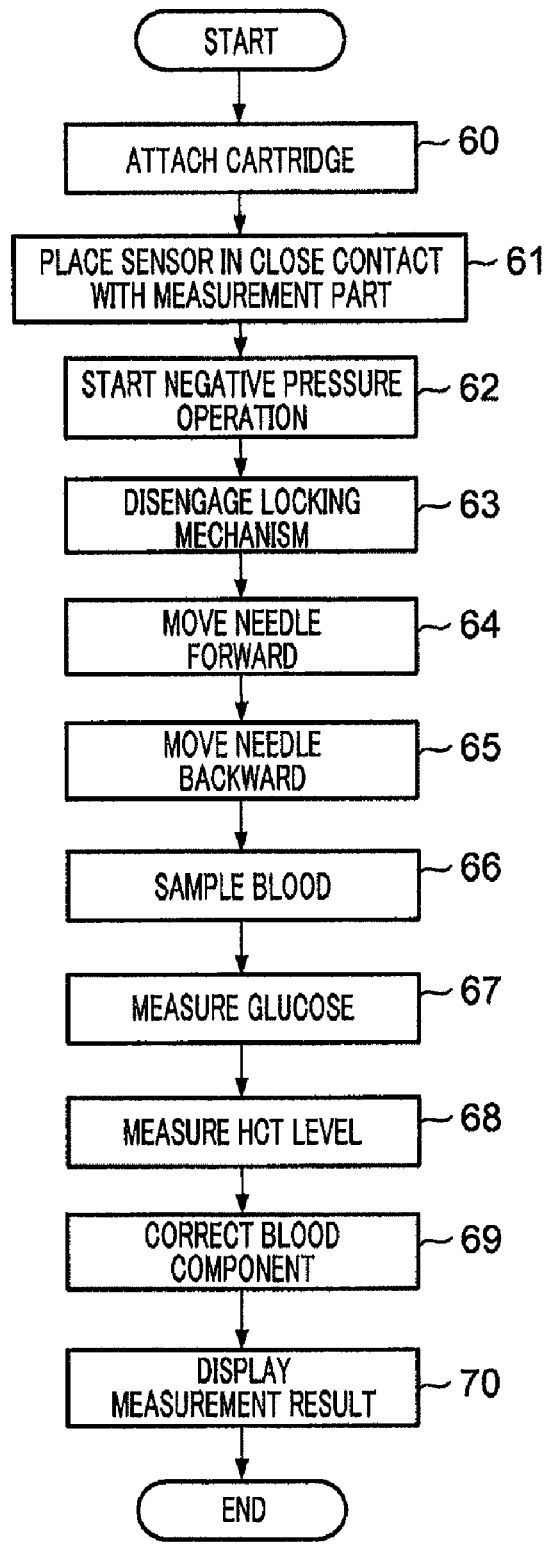
FIG. 11 shows a flow of the blood test using the blood test apparatus.

FIG. 11 shows an example of the flow of the test using blood test apparatus 20. In attaching step 60, blood sampling cartridge 22 is inserted into cylinder body 21a. By the insertion, holder 23 of blood sampling cartridge 22 is latched at slider 37, and grip part 25f of lancet 25 is held by holding part 30a of plunger 30.

In step 61, blood sensor 24 of blood sampling cartridge 22 is pressed against the part to be punctured (the skin of the patient) and forced back into opening part 21b. As a result, slider 37 presses mechanical switch 38-1 to the first position.

In step 62, the negative pressure means starts to start negative pressure operation and creates a negative pressure in cylinder body 21a. When mechanical switch 38-1 is pressed to the first position, the negative pressure means preferably starts automatically.

In step 63, the locking mechanism formed by latch convex part 31c provided in handle 31 and latch concave part 21d provided in housing 21, is released. The locking mechanism is preferably released after the negative pressure means is driven for a predetermined period, because the part to be punctured is plumped up and can be punctured easily. As described above, the part to be punctured is plumped up, and thereby the blood sensor may be further forced into opening part 21b, and slider 37 may press mechanical switch 38-1 to the second position. By displaying that mechanical switch 38-1 is pressed to the second position on display section 75, it is possible to make the timing of releasing the locking mechanism more appropriate. Further, the locking mechanism may be released automatically after mechanical switch 38-1 is pressed to the second position.

In step 64, blood collection needle 26 is propelled toward the skin of the part to be punctured via lancet 25 which interlocks with plunger 30 urged by the spring, and punctures the skin. In next step 65, blood collection needle 26 is moved backward in blood sampling cartridge 22.

In step 66, blood is sampled. The blood flowing out from the part punctured with blood collection needle 26, is guided into storing part 49 of blood sensor 24. The blood in storing part 49 flows into supply channel 47d by capillary action and is led to detecting section 40. Further, the negative pressure facilitates the inflow of blood to supply channel 47d. When the blood led to detecting section 40 reaches one electrode 43 of the electrode system as a detecting electrode, detecting section 40 determines that the amount of blood required for measurement is obtained. In this way, detecting section 40 of the blood sensor determines whether or not enough blood is obtained. Therefore, it is not necessary to over-sample blood, so that the load on the patient is reduced significantly. Further, by stopping driving of the negative pressure means after the determination, it is possible to prevent power of the battery from wasting.

In step 67, glucose is measured. After the glucose in blood and reagent 50 (containing a glucose oxidation-reduction enzyme) placed on detecting section 40 are reacted for a certain period, a voltage is applied between one electrode 42 of the electrode system as a working electrode and one electrode 44 of the electrode system as a counter electrode. The mediator in a reduction condition, produced on one electrode 42 of the electrode system by enzyme reaction, is oxidized, and its oxidation current is detected. The glucose and the glucose oxidation-reduction enzyme are normally reacted for one to ten seconds. Generally, the voltage applied in step 67 is 0.2 to 0.5 V and the time the voltage is applied is one to five seconds. The time the voltage is applied is measured by timer 79 (described later).

In step 68, the hematocrit (Hct) level is measured. A voltage is applied between one electrode 45 of the electrode system as a working electrode and one electrode 42 of the electrode system as a counter electrode. By this means, a current depending on the Hct level can be detected, and the Hct level is measured based on the detected current. The measured Hct level is used for correction in glucose measurement. The Hct level calculated from the calibration curve created in advance, of the current and the Hct level, may be used for correction. Further, the detected current may be used as is.

Generally, the voltage applied in step 68 is 2 to 3 V, and the time the voltage is applied is 0.01 to 5 seconds. In step 68, the reagent does not contact with one electrode 45 of the electrode system which is the working electrode, there is a certain interval between one electrode 45 of the electrode system and one electrode 42 of the electrode system, and only blood exists in this interval, so that an oxidation current that is not influenced by reagent 50 and that depends on the Hct level can be detected.

In step 69, blood components are corrected. That is, using the Hct level measured in step 68, the glucose content calculated in step 67 is corrected. This correction is performed based on the calibration curve (including a calibration table) created in advance. The corrected glucose content is displayed on display section 75 in blood test apparatus 20 in step 70 as a final measurement result after correction.

Used blood sampling cartridge 22 after going through steps 67, 68 and 69 of blood sugar level measurement, is replaced every measurement.

Figure 12:
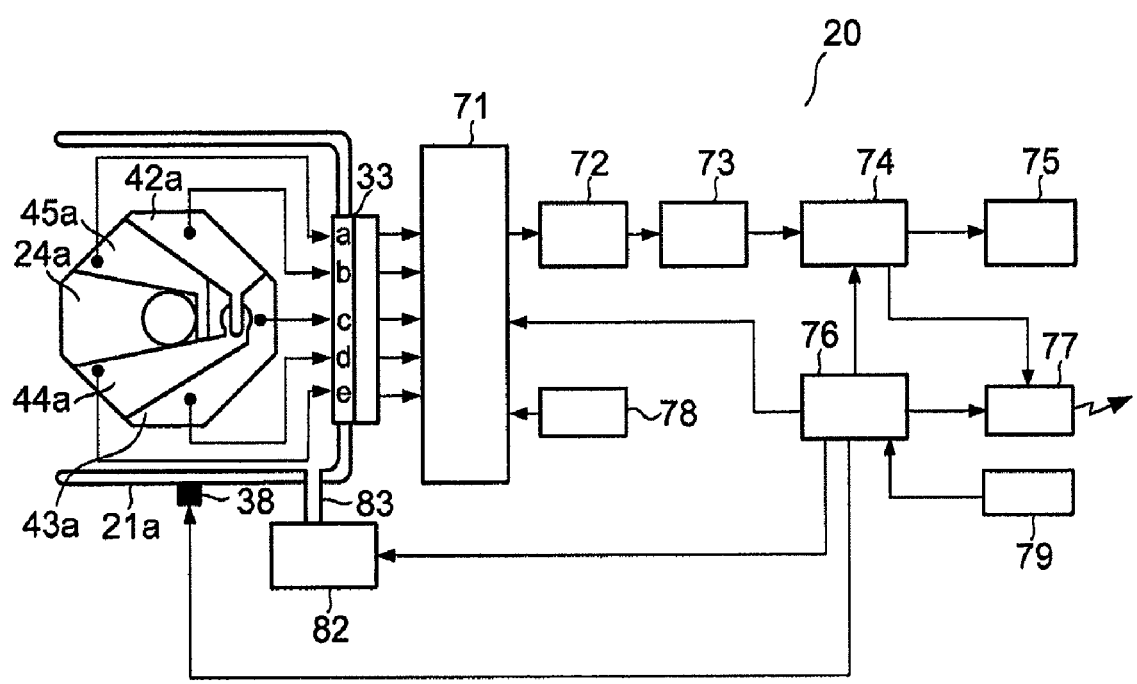
FIG. 12 is a block diagram of the blood test apparatus.
Figure 13:
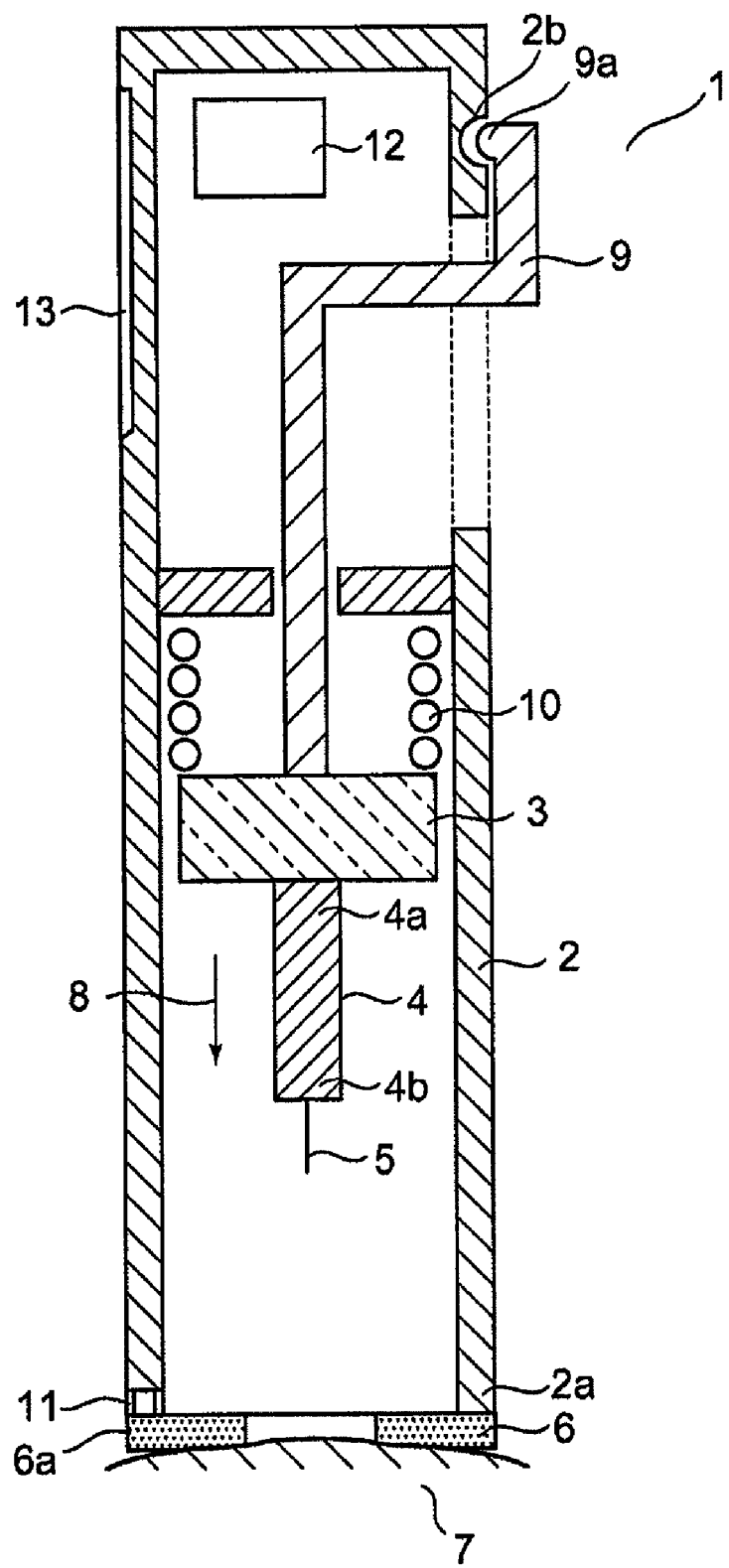
FIG. 13 is a cross-sectional view of the conventional blood test apparatus.

FIG. 12 is a block diagram of blood test apparatus 20. Blood test apparatus 20 shown in FIG. 12 has blood sensor 24a shown in FIG. 9.

Terminals 33a to 33e in FIG. 12 are connected with connecting terminals 42a to 45a (in this case, 43a includes a reference terminal and has two connection parts) of blood sensor 24a via the connectors. The terminals 33a to 33e are connected to switch circuit 71, and the output of switch circuit 71 is connected to the input of current/voltage converter 72. The output of converter 72 is connected to the input of calculating section 74 via analogue/digital converter (hereinafter A/D converter) 73. The output of calculating section 74 is connected to display section 75 (for example, a liquid crystal display). Further, reference voltage supply 78 is connected to switch circuit 71. Reference voltage supply 78 may be a ground potential.

The output of controlling section 76 is connected to a control terminal of switch circuit 71, calculating section 74, transmitting section 77 and timer 79. Further, the output of calculating section 74 is also connected to the input of transmitting section 77. The output of controlling section 76 is connected to negative pressure means 82 (for example, a vacuum generator), and the output of negative pressure means 82 communicates with the interior of cylinder body 21a via negative pressure path 83. Therefore, negative pressure means 82 can create a negative pressure inside cylinder body 21a. Further, the output of sensing means 38 (such as mechanical switch 38-1) is connected to controlling section 76, and controlling section 76 starts or stops negative pressure means 82 based on this output.

The operation of blood test apparatus 20 will be described. First, when blood sensor 24 (which may be blood sampling cartridge 22 including blood sensor 24) is attached to cylinder body 21a, the apparatus is powered on.

Before the blood test, when the blood sensor is blood sensor 24a, the following operation is performed. That is, to which of terminals 33a to 33e connecting terminals 42a to 45a are connected, is specified. By a command from controlling section 76, out of terminals 33a to 33e, a terminal where resistance with the neighboring terminal is zero, is specified. The connecting terminal connected to the specified terminal where the resistance with the neighboring terminal is zero, is determined to be connecting terminal 43a. Using one of terminals 33a to 33e connected to connecting terminal 43a as a reference, other terminals 33 are determined as terminals connected to connecting terminals 44a, 45a and 42a, in that order. In this way, after terminals 33 connected to connecting terminals 42a to 45a are determined, blood is examined. When blood sensor 24 (see FIG. 8) not having a reference terminal, is used, terminals 33 to be connected to connecting terminals 42a to 45a are determined in advance, and so this operation for the determining the connecting terminals is not necessary, and the steps are started from the following operation.

Switch circuit 71 is switched, and connecting terminal 42a of one electrode of the electrode system as a working electrode for measuring the amount of blood components is connected to current/voltage converter 72 via terminal 33b. Further, connecting terminal 43a of one electrode 43 of the electrode system which serves as a detecting electrode for detecting the inflow of blood is connected to reference voltage supply 78 via terminal 33d. A certain voltage is applied between one electrode 42 of the electrode system and one electrode 43 of the electrode system, and the apparatus enters a standby state.

In this standby state, when information that the skin of the part to be punctured is placed in an appropriate position is outputted to controlling section 76 from sensing means 38, controlling section 76 starts negative pressure means 82. After a predetermined period passes, lancet 25 is driven and puncturing is performed. Sensing means 38 may report to controlling section 76 that the skin of the part to be punctured is plumped up by a negative pressure. Controlling section 76 may display it on display section 75.

If blood from the punctured part flows into blood sensor 24a, a current flows between each electrode of electrode system 42 and 43. This current is converted to a voltage by current/voltage converter 72, and the voltage value is converted to a digital value by A/D converter 73. The digital value is outputted to calculating section 74. Calculating section 74 detects the inflow of blood based on the digital value. After the inflow of blood is detected, driving of negative pressure means 82 is stopped.

Next, glucose, which is a blood component, is measured. The glucose content is measured through the following steps. First, by the command of controlling section 76, switch circuit 71 is switched, and one electrode 42 of the electrode system, which serves as a working electrode in glucose content measurement, is connected to current/voltage converter 72 via terminal 33b. Further, one electrode 44 of the electrode system, which serves as a counter electrode in glucose content measurement, is connected to reference voltage supply 78 via terminal 33e.

While the glucose in blood and the oxidation-reduction enzyme are reacted for a certain period, current/voltage converter 72 and reference voltage supply 78 may be turned off, and, after a certain period (less than 10 seconds) passes, a certain voltage (0.2 to 0.5 V) may be applied between each electrode of electrode system 42 and 44 by a command from controlling section 76. The current flowing between each electrode of electrode system 42 and 44 is converted to a voltage by current/voltage converter 72. The converted voltage value is converted to a digital value by A/D converter 73 and outputted to calculating section 74. Calculating section 74 converts the digital value to a glucose content.

After the glucose content is measured, the Hct level is measured. The Hct level is measured through the following steps. First, by a command from controlling section 76, switch circuit 71 is switched, and one electrode 45 of the electrode system, which serves as a working electrode for measuring the Hct level, is connected to current/voltage converter 72 via terminal 33a. Further, one electrode 42 of the electrode system, which serves as a counter electrode for measuring the Hct level, is connected to reference voltage supply 78 via terminal 33b.

Then, by a command from controlling section 76, a certain voltage (2 to 3 V) is applied between each electrode of electrode system 45 and 42 from current/voltage converter 72 and reference voltage supply 78. The current flowing between each electrode of electrode system 45 and 42 is converted to a voltage by current/voltage converter 72, and the voltage value is converted to a digital value by A/D converter 73 and outputted to calculating section 74. Calculating section 74 converts the digital value to an Hct level.

Using the measured Hct level and the glucose content, and, with reference to the calibration curve or the calibration table, the glucose content is corrected with the Hct level. The corrected result is displayed on display section 75.

Further, the corrected result may be transmitted from transmitting section 77 to an injection apparatus that injects insulin (used as an example of an antidote). The result may be transmitted by radio but is preferably transmitted using optical communication which does not interfere with medical equipment. If the injection apparatus can set the dose of insulin automatically based on the measured result transmitted from transmitting section 77, the patient does not have to set the dose of insulin. Further, the dose of insulin can be set to the injection apparatus without involving an artificial means, so that it is possible to prevent setting errors.

Further, switch 38 is provided in cylinder body 21a and pressed by slider 37. Unless blood sensor 24 (which may be blood sampling cartridge 22 with blood sensor 24) is attached and forced into the attaching part and slider 37 is moved, negative pressure means 82 does not start. Therefore, negative pressure means 82 does not operate by error.

As described above, sensing means 38 may be mechanical switch 38-1, an electrical switch or an optical switch.

Mechanical switch 38-1 is pressed when the part to be punctured of the patient, pressed against the blood sensor of the blood test apparatus, contacts with tip part 21b of cylinder body 21a.

As described above, according to the blood test apparatus and blood test method of the present invention, it is possible to detect a contact between the apparatus and the skin of the patient and drive a negative pressure means automatically according to the detected output. Therefore, even when the patient holds the apparatus with one hand and performs test, the patient can hold the apparatus stably and perform measurement reliably. By releasing plunger 30 automatically after the skin is plumped up, it is possible to make the operation performed by the patient simple and realize more reliable measurement.

INDUSTRIAL APPLICABILITY

According to the blood test apparatus and blood test method of the present invention, it is possible to alleviate the load of the blood test on the patient. That is, to sample blood for test in the blood sensor, by pressing the blood sensor of the apparatus against the skin of the part to be punctured, a negative pressure means starts without special operation. Blood from the punctured part can be sampled in the blood sensor in a simple manner. Therefore, the present invention is widely applicable to medical equipment.

The present application is based on Japanese Patent Application No. 2006-022038, filed on Jan. 31, 2006, the entire content of which is expressly incorporated by reference herein.

The invention claimed is:

1. A blood test apparatus, comprising:
a housing with an opening part;
a puncturer that is provided inside the opening part;
a first sensor that detects contact between a part to be punctured and a front surface of the opening part;
a negative pressure generator that creates a negative pressure inside the opening part;
a blood sensor that samples blood flowing out from the part punctured with the puncturer after the negative pressure is created inside the opening part by the negative pressure generator; and
a measuring circuit that measures a signal obtained from the blood sensor to analyze components in the blood,
wherein:
the blood sensor is positioned to project from the front surface of the opening part and is mounted for movement in and out of the housing through the opening part;
the first sensor is configured to detect that the blood sensor is forced into the opening part by the part to be punctured; and
the negative pressure generator starts when the first sensor detects that the blood sensor is forced into the opening part.

2. The blood test apparatus according to claim 1, wherein the negative pressure generator stops when the first sensor detects a non-contact between the part to be punctured and the front surface of the opening part.

3. The blood test apparatus according to claim 1, wherein the first sensor comprises a mechanical switch provided in the opening part that is pressed when the blood sensor is forced into the opening part by the part to be punctured.

4. The blood test apparatus according to claim 1, wherein the first sensor comprises an electrical switch or an optical switch provided in the opening part that detects an electrical change or an optical change caused when the blood sensor is forced into the opening part by the part to be punctured.

5. The blood test apparatus according to claim 1, further comprising a second sensor that detects a plumpness of the part to be punctured by the negative pressure.

6. The blood test apparatus according to claim 5, wherein the puncturer performs puncturing after the second sensor detects a plumpness of the part to be punctured.

7. The blood test apparatus according to claim 5, wherein the second sensor detects that the blood sensor is forced into the opening part by the plumped up part to be punctured.

8. The blood test apparatus according to claim 1, wherein:
the blood sensor comprises:
a storage into which blood flowing out from the part punctured with the puncturer is directed;
a supply channel, one end of the supply channel communicates with the storage, and into which the blood in the storage flows;
a detector which is provided in the supply channel, and in which an electrode system is provided; and
an air hole which communicates with an other end of the supply channel,
wherein the negative pressure generator creates a negative pressure in the supply channel via the air hole to facilitate an inflow of the blood in the storage to the supply channel.

9. The blood test apparatus according to claim 5, wherein:
the blood sensor comprises:
a storage into which blood flowing out from the part punctured with the puncturer is directed;
a supply channel, one end of the supply channel communicates with the storage, and into which the blood in the storage flows;
a detector which is provided in the supply channel, and in which an electrode system is provided; and
an air hole which communicates with an other end of the supply channel,
wherein the negative pressure generator creates a negative pressure in the supply channel via the air hole to facilitate an inflow of the blood in the storage to the supply channel.

10. The blood test apparatus according to claim 8, wherein the negative pressure generator stops when the electrode system detects an inflow of the blood to the supply channel.

11. The blood test apparatus according to claim 1, wherein the puncturer comprises:
a lancet, one end of which is held by a plunger that moves back and forth inside the housing; and
a blood collection needle attached to an other end of the lancet.

12. The blood test apparatus according to claim 1, wherein:
the blood sensor together with a holder that holds the blood sensor comprises an integrated blood sampling cartridge; and
the blood sampling cartridge is removably attached to the opening part.

13. The blood test apparatus according to claim 1, wherein:
the puncturer, the blood sensor and a holder comprise an integrated blood sampling cartridge;
the puncturer comprises:
a lancet, one end of which is held by a plunger that moves back and forth inside the housing; and
a blood collection needle attached to an other end of the lancet; and
the blood sampling cartridge is removably attached to the opening part.

14. The blood test apparatus according to claim 13, wherein the puncturer and the blood sensor in the blood sampling cartridge attached to the opening part are mounted for movement relative to each other.

15. The blood test apparatus according to claim 13, wherein the first sensor detects a move of the blood sensor of the blood sampling cartridge attached to the opening part, toward inside the opening part.

16. A method for examining blood with the blood test apparatus according to claim 1, comprising:
   detecting contact between the part to be punctured and the front surface of the opening part, by the first sensor;
   creating a negative pressure inside the opening part by the negative pressure generator;
   puncturing the part to be punctured by the puncturer;
   sampling blood flowing out from the punctured part in the blood sensor; and
   analyzing components in the sampled blood.

17. The method according to claim 16, further comprising detecting a non-contact between the part of the skin to be punctured and the front surface of the opening part by the first sensor and stopping the negative pressure generator.

18. A method for examining blood with the blood test apparatus according to claim 8, comprising:
   detecting contact between the part to be punctured and the front surface of the opening part, by the first sensor;
   creating a negative pressure inside the opening part by the negative pressure generator;
   puncturing the part to be punctured by the puncturer;
   sampling blood flowing out from the punctured part in the blood sensor;
   detecting an inflow of the blood to the blood supply channel by the electrode system and stopping the negative pressure generator; and
   analyzing components in the sampled blood.

19. A method for examining blood with the blood test apparatus according to claim 9, comprising:
   detecting contact between the part to be punctured and the front surface of the opening part, by the first sensor;
   creating a negative pressure in the opening part by the negative pressure generator;
   detecting a plumpness of the part to be punctured, by the second sensor;
   puncturing the part to be punctured by the puncturer;
   sampling blood flowing out from the punctured part in the blood sensor;
   detecting an inflow of the blood to the blood supply channel by the electrode system and stopping the negative pressure generator; and
   analyzing components in the sampled blood.

* * * * *